United States Patent [19]
Durvasula

[11] Patent Number: 4,599,445
[45] Date of Patent: Jul. 8, 1986

[54] PROCESS FOR BENZOPHENONE TETRACARBOXYLIC ACID

[75] Inventor: Visweswara R. Durvasula, Cheshire, Conn.

[73] Assignee: The Dow Chemical Company, Midland, Mich.

[21] Appl. No.: 652,922

[22] Filed: Sep. 21, 1984

Related U.S. Application Data

[62] Division of Ser. No. 460,177, Jan. 24, 1983, Pat. No. 4,485,247.

[51] Int. Cl.[4] .................... C07C 51/09; C07D 307/88
[52] U.S. Cl. ...................................... 562/419; 549/310
[58] Field of Search ........................ 562/419; 549/310

[56] References Cited

U.S. PATENT DOCUMENTS

| | | | |
|---|---|---|---|
| 2,050,657 | 8/1936 | Greune | 562/419 |
| 2,806,059 | 9/1957 | Bruson et al. | 562/412 |
| 2,833,816 | 5/1958 | Saffer et al. | 260/524 |
| 2,999,879 | 9/1961 | Broich et al. | 562/419 |
| 3,038,940 | 6/1962 | Serres et al. | 260/590 |
| 3,078,279 | 2/1963 | McCracken et al. | 260/346.3 |
| 3,089,906 | 5/1963 | Saffer et al. | 260/524 |
| 3,162,683 | 12/1964 | Jones et al. | 260/524 |
| 3,652,598 | 3/1972 | Broadhead | 260/346.3 |
| 4,173,573 | 11/1979 | Schulz et al. | 260/346.4 |
| 4,323,700 | 4/1982 | Kondo et al. | 562/460 |

OTHER PUBLICATIONS

Fieser & Fieser, *Organic Chemistry*, 3rd ed., 1956, Reinhold Publ. Co., N.Y., pp. 656–663.

*Primary Examiner*—Howard T. Mars
*Assistant Examiner*—Patricia M. Scott
*Attorney, Agent, or Firm*—J. S. Rose

[57] ABSTRACT

A method is described for autoxidizing particular ortho-dialkyl substituted aromatic compounds using a particular type of solvent which gives rise to the formation of 3-alkanoyloxyphthalide compounds, some of which are novel.

The phthalides in turn are ionically oxidized to their corresponding aromatic polycarboxylic acids.

Combination of the two methods provides a means for converting ortho dialkyl substituted aromatic compounds directly to the corresponding polycarboxylic acids in higher yields and at generally lower overall temperatures and reaction conditions compared to prior art methods.

Polycarboxylic acids so obtained are known to be useful in the preparation of alkyds, polyesters, and the like, and, particularly, in the formation of the corresponding acid anhydrides which are used in the preparation of organic high temperature polymers such as polyamides, polyamideimides, and polyimides.

10 Claims, No Drawings

PROCESS FOR BENZOPHENONE TETRACARBOXYLIC ACID

This application is a division of application Ser. No. 460,177 filed Jan. 24, 1983, now U.S. Pat. No. 4,485,247.

BACKGROUND OF THE INVENTION

1. Field of the Invention

This invention relates to novel oxidation methods and is more particularly concerned with the ionic oxidation of certain phthalide moieties to aromatic polycarboxylic acids, a method for the autoxidation of certain aromatic compounds having ortho dialkyl substituents to said phthalides, particular novel diphthalides produced therefrom, and an improved method for converting said aromatic compounds to said polycarboxylic acids by the combination of the above two oxidation methods.

2. Description of the Prior Art

Autoxidation processes involving the conversion of a wide variety of polyalkyl-substituted aromatic compounds to the corresponding aromatic carboxylic acids have been extensively studied and documented in the prior art. Generally speaking, all of these methods produce directly the fully oxidized carboxylic acids.

Bruson et al in U.S. Pat. No. 2,806,059 disclose that diaryl methanes or diaryl ketones in which the aryl rings are substituted by alkyl groups and combinations of alkyl groups with carbonyl containing groups (i.e. aldehyde, acid, ester) can be oxidized in acetic acid solution with oxygen using, typically, cobalt salts as catalysts and aliphatic ketones as promoters, to the corresponding carboxylic acids.

Saffer et al in U.S. Pat. No. 2,833,816 disclose the preparation of aromatic polycarboxylic acids by oxidizing polyalkyl aromatic compounds with oxygen in solution (preferably acetic acid) using a heavy metal oxidation catalyst in combination with bromine either in elemental, combined or ionic form.

In U.S. Pat. No. 3,038,940, Serres et al disclose the oxidation of diaryl substituted methylene groups to the corresponding diaryl ketones in a solution of an oxidation resistant monocarboxylic acid in the presence of the combination of a heavy metal oxidation catalyst and bromine.

In U.S. Pat. No. 3,089,906 Saffer et al disclose a process carried out above atmospheric pressure wherein alkyl-substituted aromatic compounds are oxidized in solution in the presence of a heavy metal oxidation catalyst and a source of bromine.

Broadhead in U.S. Pat. No. 3,652,598 discloses the oxidation of various 2,2',3,3'- and 3,3',4,4'-tetraalkyldiphenylmethanes to the corresponding 2,2',3,3'- and 3,3',4,4'-tetracarboxylic acids by oxidation of the substrate with oxygen in acetic acid solution using, inter alia, manganese bromide as catalyst as taught in U.S. Pat. No. 2,833,816 cited supra.

Jones et al (U.S. Pat. No. 3,162,683) in reporting on the oxidation of alkyl aromatic compounds in the presence of perhalogenated aliphatic carboxylic acids noted, in the case of o-xylene, that o-toluic acid was formed along with varying proportions of phthalide. However, neither the complete oxidation of xylene to phthalide, nor the oxidation of both methyls of the xylene to carboxyl groups was found.

In the typical prior art cited supra, the methods for oxidizing the polyalkyl-substituted aromatic compounds provide satisfactory yields of the aromatic acids when the alkyl groups are not on adjacent carbon atoms of the same aromatic ring. However, where the alkyl groups are in ortho relationship to each other (i.e. on adjacent carbon atoms of the aromatic ring) the overall yields of the fully oxidized products produced by these prior art methods are low.

Apparently, the oxidation of the first alkyl group to a carboxylic group has the effect of deactivating the adjacent alkyl group thereby slowing down, or stopping completely, the oxidation of the second alkyl. Generally speaking, product mixtures are obtained which contain mono-, di-, tri-, or tetracids depending on the starting number of alkyl groups and the extent of oxidation. For example, when oxidizing the 2,2',3,3'- or 3,3',4,4'-tetraalkyldiphenylmethanes set forth in the process described in U.S. Pat. No. 3,652,598 cited supra the corresponding pure tetracids are not obtained but rather mixtures comprised of the mono-, di-, tri-, and tetracids. Consequently, yields of the desired tetracid are lowered and purification steps become complicated.

These disadvantages have been partially overcome in the prior art by resorting to much more rigorous oxidation conditions in terms of the reagents employed as typically disclosed in U.S. Pat. Nos. 3,078,279 and 4,173,573 which call for the use of nitric acid at elevated temperatures and pressures (i.e. 110° C. to 350° C. and up to 500 pounds per square inch). While yields of desired tetracids are superior to those from the other methods discussed above, the more stringent operating conditions required because of the nitric acid under the reaction conditions of high temperature and pressure make for an expensive and somewhat dangerous procedure.

Surprisingly, it has now been discovered that a certain class of phthalide compounds can be oxidized to the corresponding aromatic carboxylic acids under mild ionic oxidizing conditions of aqueous alkaline hypohalite. The yields and product purity in regard to fully oxidized products are superior to the direct autoxidations of the prior art discussed above yet the conditions are far less stringent than those prior art methods which employ nitric acid.

The only reference of which I am aware concerning a related method is U.S. Pat. No. 4,323,700 wherein a different class of phthalides are oxidized under ionic conditions to products unrelated to the instant orthodicarboxylic acids.

Further, it has also been discovered that, when a certain class of aromatic compounds having dialkyl groups substituted on adjacent carbon atoms of an aromatic ring are subjected to autoxidation techniques similar to those described above in the prior art but differing in one key respect, the result is not the direct formation of the corresponding polycarboxylic acid but rather of an alkanoyloxyphthalide. The key difference is the carrying out of the autoxidation in a solution of an aliphatic carboxylic acid anhydride. The anhydride plays more of a role than just a solvent and this role will be discussed in detail below.

Furthermore, the above steps can be combined to provide an improved method for oxidizing the aromatic compounds referred to above to the corresponding aromatic polycarboxylic acids in yields and product purity which exceed the prior art direct autoxidation methods while at the same time avoiding the use of nitric acid.

In a further unexpected advantage to flow from the combination of the two methods in accordance with the present invention, it has been found that the ionic oxidation proceeds under even milder conditions (circa 20° C. and below) when the crude reaction mixture from the autoxidation is employed without purification other than removal of solvent when compared to oxidizing an isolated purified form of the phthalide. This aspect of the present invention will be discussed in detail below.

SUMMARY OF THE INVENTION

This invention comprises a method for converting 3-alkanoyloxyphthalides selected from the formulae consisting of

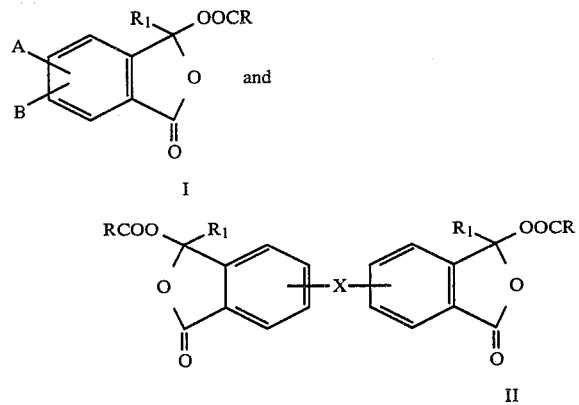

to the corresponding polycarboxylic acids having the formulae

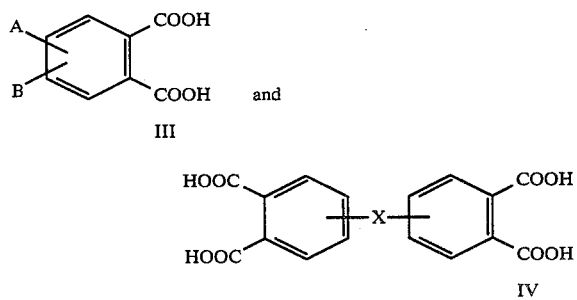

respectively, wherein R represents lower-alkyl, $R_1$ is selected from the group consisting of hydrogen and linear lower-alkyl, A and B taken separately are independently selected from the group consisting of hydrogen and inert substituents, A and B taken together represent an aromatic nucleus fused to the phenyl ring, and X is selected from the group consisting of —CO—, —SO$_2$—, —O—, and a single bond, said method comprising oxidizing said 3-alkanoyloxyphthalide with aqueous alkaline hypohalite.

This invention also comprises a method for converting aromatic compounds selected from the formulae consisting of

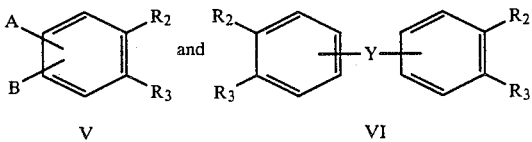

to the corresponding 3-alkanoyloxyphthalides defined by (I) and (II) above wherein $R_2$ and $R_3$ are independently selected from linear lower-alkyl, and the $R_1$ linear lower-alkyl has one less methylene than the corresponding $R_2$ or $R_3$ group, and Y is selected from the group consisting of —CO—, —SO$_2$—, —O—, a single bond, and —CH$_2$—, and A and B have the same meaning as set forth above, said method comprising autoxidizing said aromatic compound in a solution comprising an anhydride of an aliphatic monocarboxylic acid having 2 to 8 carbon atoms with oxygen in the presence of a heavy metal oxidation catalyst and a promoter.

This invention also comprises a method for the conversion of the 3-alkanoyloxyphthalides (I) and (II) to the corresponding polycarboxylic acids (III) and (IV) wherein said starting compounds (I) and (II) are prepared by the autoxidation method defined above for the conversion of the aromatic compounds (V) and (VI) to (I) and (II) respectively.

This invention also comprises the novel 3-alkanoyloxyphthalides defined by formula (II) above.

The term "lower-alkyl" means alkyl having from 1 to 8 carbon atoms, inclusive, such as methyl, ethyl, propyl, butyl, amyl, hexyl, heptyl, octyl, and isomeric forms thereof.

The term "linear lower-alkyl" means alkyl having the same carbon atom limitation set forth above but limited to the linear alkyl groups recited above.

The term "inert substituent" means any substituent that does not react with the carboxylic acid products or phthalides or otherwise interfere with the oxidation methods and is typically inclusive of both lower and linear lower-alkyl defined above; halo, i.e., chloro, bromo, fluoro, and iodo; alkoxy from 1 to 8 carbon atoms, inclusive, such as methoxy, ethoxy, propoxy, butoxy, pentyloxy, hexyloxy, heptyloxy, octyloxy, and the like, including isomeric forms thereof; cyano; —SO$_3$H; —COOH; —COOR wherein R represents lower-alkyl, aryl, aralkyl, cycloalkyl, and the like.

The term "aromatic nucleus" means another aromatic hydrocarbon residue fused to the phenyl ring such that the resulting fused ring is typically inclusive of naphthalene, phenanthrene, anthracene, fluorene, acenaphthene, and the like.

The term "heavy metal oxidation catalyst" means a heavy metal capable of existence in variable valence states and in either elemental, combined, or ionic form which is capable of catalyzing the autoxidation of a lower-alkyl group substituted on an aromatic nucleus to a carboxylic acid group, said heavy metals being inclusive of manganese, cobalt, nickel, chromium, vanadium, molybdenum, tungsten, tin, and cerium.

The term "promoter" means an additive which, in combination with the heavy metal oxidation catalyst, is capable of increasing the rate of the autoxidation described above.

The polycarboxylic acid products (III) and (IV) produced in accordance with the present invention are useful as intermediates in the production of polyester polymers and alkyds but find particular utility in the production of the corresponding anhydrides which in turn serve as intermediates in the preparation of polyimides, polyamides, polyamideimides, curatives for epoxy resins, and the like. Particularly useful in this regard are the dianhydrides prepared from the tetracarboxylic acids (IV) produced in accordance with the present invention.

The phthalide compounds find particular utility as starting materials for the corresponding polycarboxylic acids (III) and (IV) which can be used in the applications noted above.

DETAILED DESCRIPTION OF THE INVENTION

The individual methods in accordance with the present invention will be referred to hereinafter as Method A and Method B. The combination of the two methods, which combination is also in accordance with the present invention, can be represented by the following schematic equation sequence starting with a simple ortho-dialkyl-substituted benzene for purposes of illustration.

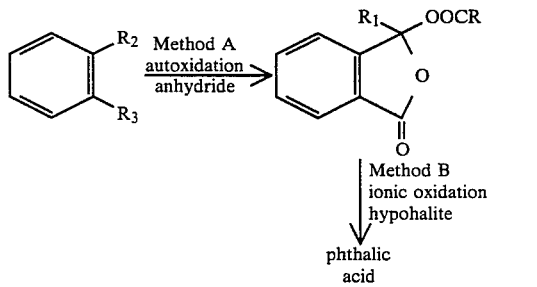

wherein $R_2$, $R_3$, $R_1$, and R are defined above. It is to be understood that the ortho-dialkyl-benzene is representative of (V) and (VI) and the phthalide is representative of (I) and (II) while the phthalic acid is representative of (III) and (IV) all as defined above.

Method A

The autoxidation of the aromatic compounds (V) and (VI) to the corresponding 3-alkanoyloxyphthalides (I) and (II) is carried out in solution using oxygen or an oxygen containing gas such as air in the presence of, known heavy metal oxidation catalysts and promoters. However, the novelty in the present Method A resides in the choice of solvent in which to carry out the solution oxidation.

Surprisingly, the use of the class of acid anhydrides defined above in which to carry out the solution oxidation results in a dramatic change in the course of the autoxidation and the resultant products obtained in comparison to prior art methods. Instead of the alkyl groups $R_2$ and $R_3$ being oxidized directly to carboxylic acids, a 3-alkanoyloxyphthalide is formed. At the same time the anhydride solvent acts as both a dehydrating agent and acetylating agent such that the alkanoyl radical (R) appearing on the phthalide ring corresponds to the alkanoyl grouping of the anhydride.

While not wishing the present invention to be bound by any theoretical considerations but only by the claims appended hereinbelow, it is believed that approximately 3 molar equivalents of anhydride are required per molar equivalent of ortho-dialkyl groups ($R_2$ and $R_3$) in (V) and (VI). The pathway from (V), (VI) to (I), (II) can be represented schematically as follows using the same ortho-dialky-substituted benzene model compound as above and starting the autoxidation at the $R_2$ alkyl group.

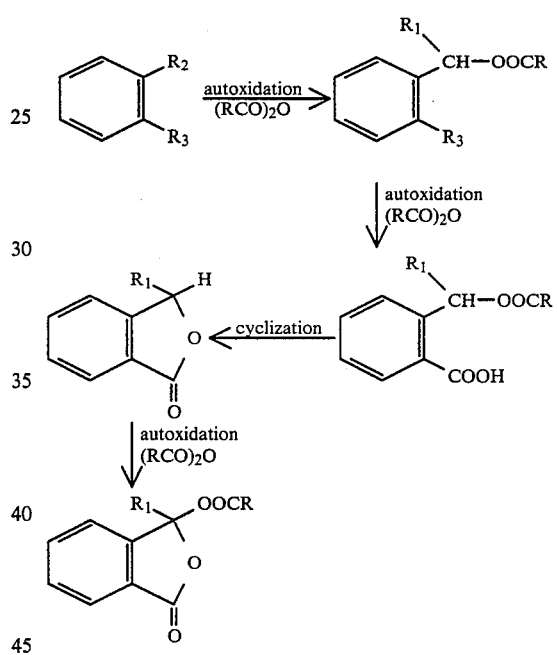

It will be obvious to one skilled in the art that, when the linear lower-alkyl group $R_2$ (or $R_3$ whichever reacts first) is other than methyl, this group is oxidized at the methylene adjacent to the aromatic ring, and the lower-alkyl group $R_1$, in the resulting phthalide represents alkyl having one less methylene than $R_2$.

In this connection, it should be noted that geometric isomer forms of the 3-alkanoyloxyphthalides (I) and (II) can be formed in accordance with the present Method A, depending on which group $R_2$ or $R_3$ is oxidized first, and, of course, on the nature of the substituents, if any, on the benzene ring which would provide the necessary molecular conformation with the phthalide to result in isomer formation. The autoxidation of (V) and (VI) in accordance with the present invention produces the phthalides (I) and (II) as the major proportion of the reaction product. At the same time, the fully oxidized polycarboxylic acid in the form of the anhydride is formed in a minor proportion. Generally speaking, the phthalides are formed in at least a 60 percent molar proportion over the polycarboxylic acid anhydride. Notwithstanding, the overall autoxidation process provides fully oxidized products whether in the form of the phthalides or the fully oxidized carboxylic acid anhydrides with little or no partially oxidized products. Furthermore, overall conversions and yields are very high with conversions being in excess of 90 percent and product yields being well over 90 percent, particularly when polycarboxylic acids are the ultimately desired product.

A preferred class of anhydrides for use in the present invention is that of an aliphatic monocarboxylic acid having 2 to 4 carbon atoms, and, most preferably, acetic anhydride and propionic anhydride.

Generally speaking, the anhydride is employed in quantities sufficient to act as a solvent for the compounds (V) and (VI). The specific amount which may be optimum for any given starting compound can be easily determined by trial and error. However, as noted above, and, because it does play a chemical role in the overall process, it is advantageous to employ the anhydride in an amount such that at least 3 molar equivalents per molar equivalent of ortho-dialkyl groups in (V) and (VI) are present wherein the equivalent weight of the ortho-dialkyl compounds are defined by the molecular weight divided by the number of pairs of ortho-dialkyl groups contained therein.

Preferably, the anhydride is employed in an excess of from about 10 to about 500 molar percent over that set forth above, and, most preferably, from about 10 to about 60 percent excess.

A preferred solution environment for the autoxidation in accordance with the present invention comprises a combination of the above defined anhydrides with an aliphatic monocarboxylic acid having 2 to 8 carbon atoms. A preferred combination within this class comprises an anhydride having 2 to 4 carbons with the corresponding monocarboxylic acid; most preferred are the combinations of acetic acid with acetic anhydride and propionic acid with propionic anhydride.

The proportions of anhydride and monocarboxylic acid are not critical so long as the minimum requirements for the anhydride set forth above are present in any given combination. Advantageously, the acid can be employed in a weight range of from about 10 to about 500 percent of the weight of the anhydride, preferably about 50 to about 250 percent.

Illustrative of the aliphatic monocarboxylic acid anhydrides are acetic anhydride, propionic anhydride, butyric anhydride, isobutyric anhydride, valeric anhydride, caproic anhydride, heptylic anhydride, caprylic anhydride, and the like. Preferred amongst the anhydrides are acetic anhydride, propionic anhydride, and butyric anhydride.

Illustrative of aliphatic carboxylic acids are acetic, propionic, butyric, isobutyric, valeric, caproic, heptylic, caprylic, and the like. Preferred amongst the acids are acetic, propionic, and butyric.

A particularly preferred combination comprises acetic anhydride and acetic acid.

A preferred aromatic compound to be autoxidized in accordance with the present invention has the formula (VI) wherein $R_2$ and $R_3$ are methyl in all cases and accordingly, the correspondingly produced (II) has $R_1$ equal to hydrogen.

Illustrative of the aromatic compounds (V) are o-xylene, o-diethylbenzene, o-dipropylbenzene, o-dibutylbenzene, o-dipentylbenzene, o-dihexylbenzene, o-diheptylbenzene, o-dioctylbenzene, 1-methyl-2-ethylbenzene, 4-chloro-o-xylene, 4-methoxy-o-xylene, 4-bromo-o-xylene, 3,4-dimethylbenzoic acid; pseudocumene, durene, and the like; 2,3-dimethylnaphthalene, 2,3-diethylnaphthalene, 2,3-dimethyl-5-chloronaphthalene, 2,3,6,7-tetramethylnaphthalene, 1,2,5,6-tetramethylnaphthalene, 1,2-dimethylacenaphthene, 9,10-dimethylphenanthrene, 2,3-dimethylfluorene, 2,3,6,7-tetramethylfluorene, and the like.

Illustrative of the aromatic compounds (VI) are 2,2',3,3'-tetramethylbiphenyl, 2,2',3,3'-tetraethylbiphenyl, 2,2',3,3'-tetrabutylbiphenyl, 3,3',4,4'-tetramethylbiphenyl, 3,3',4,4'-tetraethylbiphenyl, 3,4-dimethyl-3',4'-diethylbiphenyl, 2,2',3,3'-tetramethyldiphenylmethane, 2,2',3,3'-tetraethyldiphenylmethane, 2,2',3,3'-tetrabutyldiphenylmethane, 2,2',3,3'-tetraoctyldiphenylmethane, 2,3-dimethyl-2',3'-diethyldiphenylmethane, 3,3',4,4'-tetramethyldiphenylmethane, 3,3',4,4'-tetraethyldiphenylmethane, 2,2',3,3'-tetramethyldiphenyl ether, 2,2',3,3'-tetraethyldiphenyl ether, 3,3',4,4'-tetramethyldiphenyl ether, 3,3',4,4'-tetraethyldiphenyl ether, 2,2',3,3'-tetramethyldiphenyl sulfone, 2,2',3,3'-tetraethyldiphenyl sulfone, 3,3',4,4'-tetramethyldiphenyl sulfone, 3,3',4,4'-tetraethyldiphenyl sulfone, 3,3',4,4'-tetrabutyldiphenyl sulfone, 3,4-dimethyl-3',4'-diethyldiphenyl sulfone, 2,2',3,3'-tetramethylbenzophenone, 2,2',3,3'-tetraethylbenzophenone, 3,3',4,4'-tetramethylbenzophenone, 3,3',4,4'-tetraethylbenzophenone, 3,3'-dimethyl-4,4'-diethylbenzophenone, and the like.

In a preferred embodiment of the Method A in accordance with the present invention the aromatic compounds set forth above under (VI) are converted to the corresponding novel phthalides (II). Particularly preferred embodiments are those wherein (VI) are the tetralkyldiphenyl sulfones and the tetralkylbenzophenones.

Typical, but not limiting of the 3-alkanoyloxyphthalides (I) prepared in accordance with the present invention are 3-acetoxyphthalide, 3-methyl-3-acetoxyphthalide, 3-ethyl-3-acetoxyphthalide, 3-propyl-3-acetoxyphthalide, 3-butyl-3-acetoxyphthalide, 3-amyl-3-acetoxyphthalide, 3-hexyl-3-acetoxyphthalide, 3-heptyl-3-acetoxyphthalide, 3-propanoyloxyphthalide, 3-butanoyloxyphthalide, 3-pentanoyloxyphthalide, 3-hexanoyloxyphthalide, 3-heptanoyloxyphthalide, 3-octanoyloxyphthalide, 3-methyl-3-propanoyloxyphthalide, 3-butyl-3-propanoyloxyphthalide, 5-chloro-3-acetoxyphthalide, 5-bromo-3-acetoxyphthalide, 5-carboxy-3-acetoxyphthalide, the corresponding bis-3-acetoxyphthalide derived from durene, the corresponding 3-acetoxyphthalide derived from 2,3-dimethylnaphthalene, the corresponding bis-3-acetoxyphthalide derived from 2,3,6,7-tetramethylnaphthalene, the corresponding 3-acetoxyphthalide derived from 1,2-acenaphthene, and the like.

Typical but not limiting of the 3-alkanoyloxyphthalides (II) are 4,4'-bis(3-acetoxyphthalide), 4,7'-bis(3-acetoxyphthalide), 7,7'-bis(3-acetoxyphthalide), 4,4'-bis(3-propanoyloxyphthalide), 4,7'-bis(3-propanoyloxyphthalide), 7,7'-bis(3-propanoyloxyphthalide), 5,5'-bis(3-acetoxyphthalide), 5,6'-bis(3-acetoxyphthalide), 6,6'-bis(3-acetoxyphthalide), 4,4'-methylenebis(3-acetoxyphthalide), 4,7'-methylenebis(3-acetoxyphthalide), 7,7'-methylenebis(3-acetoxyphthalide), 7,7'-methylenebis(3-propanoyloxyphthalide), 5,5'-methylenebis(3-acetoxyphthalide), 5,6'-methylenebis(3-acetoxyphthalide), 6,6'-methylenebis(3-acetoxyphthalide), 4,4'-oxybis(3-acetoxyphthalide), 4,7'-oxybis(3-acetoxyphthalide), 7,7'-oxybis(3-acetoxyphthalide), 5,5'-oxybis(3-acetoxyphthalide), 5,6'-oxybis(3-acetoxyphthalide), 6,6'-oxybis(3-acetoxyphthalide), 4,4'-sulfonylbis(3-acetoxyphathalide), 4,7'-sulfonylbis(3-acetoxyphthalide), 7,7'-sulfonylbis(3-acetoxyphthalide), 4,4'-sulfonylbis(3-propanoyloxyphthalide), 4,7'-sulfonylbis(3-butanoyloxyphthalide), 4,7'-sulfonylbis(3-pentanoyloxyphthalide), 7,7'-sulfonylbis(3-propanoyloxyphthalide), 7,7'-sulfonylbis(3-butanoyloxyphthalide), 7,7'-sulfonylbis(3-pentanoyloxyphthalide), 7,7'-sulfonylbis(3-hexanoyl-oxyphthalide), 5,5'-sulfonylbis(3-acetoxyphthalide), 5,5'-sulfonylbis(3-propanoyloxyphthalide), 5,5'-sulfonylbis(3-butanoyloxyphthalide), 5,5'-sulfonylbis(3-pentanoyloxyphthalide), 5,5'-sulfonylbis(3-hexanoyloxyphthalide), 5,5'-sulfonylbis(3-heptanoyloxyphthalide), 5,6'-sulfonylbis(3-acetoxyphthalide), 5,6'-sulfonylbis(3-propanoyloxyphthalide), 5,6'-sulfonylbis(3-butanoyloxyphthalide), 6,6'-sulfonylbis(3-acetoxyphthalide), 6,6'-sulfonylbis(3-propanoyloxyphthalide), 4,4'-carbonylbis(3-acetoxyphthalide), 4,4'-carbonylbis(3-propanoyloxyphthalide), 4,4'-carbonylbis(3-butanoyloxyphthalide), 4,4'-carbonylbis(3-pentanoyloxyphthalide), 4,7'-carbonylbis(3-acetoxyphthalide), 4,7'-carbonylbis(3-propanoyloxyphthalide), 4,7'-carbonylbis(3-butanoyloxyphthalide), 7,7'-carbonylbis(3-acetoxyphthalide), 7,7'-carbonylbis(3-propanoyloxyphthalide), 5,5'-carbonylbis(3-acetoxyphthalide), 5,5'-carbonylbis(3-propanoyloxyphthalide), 5,5'-carbonylbis(3-butanoyloxyphthalide), 5,5'-carbonylbis(3-pentanoyloxyphthalide), 5,6'-carbonylbis(3-acetoxyphthalide), 5,6'-carbonylbis(3-butanoyloxyphthalide), 5,6'-carbonylbis(3-pentanoyloxyphthalide), 6,6'-carbonylbis(3-acetoxyphthalide), 6,6'-carbonylbis(3-propanoyloxyphthalide), 6,6'-carbonylbis(3-butanoyloxyphthalide), 6,6'-carbonylbis(3-pentanoyloxyphthalide), and the like.

Preferred amongst the 3-alkanoyloxyphthalides set forth above as intermediates in the further oxidation to the polycarboxylic acids are those novel classes of diphthalides falling within formula (II). Particularly preferred amongst those set forth above are the sulfonylbis(phthalides) and carbonylbis(phthalides).

The autoxidation process is carried out in the presence of any type of heavy metal oxidation catalyst known in the art and defined above. Although the heavy metal can be used in its elemental finely divided form, or other combined forms, it has been found advantageous to employ the metals in the forms in which the metal ion itself is provided.

Typical of the heavy metal catalysts which can be used in accordance with the present invention are manganese acetate, cobalt acetate, nickel acetate, chromium acetate, vanadium acetate, molybdenum acetate, tin acetate, ammonium molybdate, cobalt hydroxy quinolate.

Preferred are the heavy metal acetates and particularly preferred is cobaltous acetate.

The amount of catalyst which is most efficacious and economical in any given reaction can be easily determined by one skilled in the art by trial and error testing. Generally speaking, the catalyst is employed in an amount of from about 1 to about 15 mole percent based on the moles of starting aromatic compound employed.

Preferably, the catalyst is employed in an amount from about 4 to about 10 mole percent.

The promoter as defined above can be any additive which is found to increase the overall autoxidation rate or otherwise assist in the process.

Typical, but not limiting, of promoters are methyl ethyl ketone, ozone, zirconyl acetate, sodium acetate, potassium acetate, barium acetate, zinc acetate, potassium sulfate, titanium dioxide, sources of bromine such as hydrogen bromide, ammonium bromide, potassium bromate, tetrabromoethane, benzyl bromide, potassium bromide, sodium bromide, and the like. Also, the bromine can be provided in the same compound as the catalyst itself such as manganese bromide and the like.

Preferred as promoters are the compounds providing a source of bromine, particularly ionic bromine, such as potassium bromide, sodium bromide, and the like.

The amount of promoter to be employed can vary within wide limits and the amount of any given promoter providing the most efficacious results can be easily determined by trial and error.

Generally speaking, the promoter is employed in an amount of from about 1 to about 15 mole percent based on the moles of starting aromatic compound employed.

In most cases it is advantageous to employ the catalyst and promoter in equimolar proportions.

The autoxidation reaction is carried out readily using typical reaction methods and apparatus described in the prior art.

Any type of reaction vessel can be employed ranging from laboratory glassware which is open to atmospheric pressure to sealed autoclaves capable of withstanding high pressures. The particular apparatus to be used depends largely on whether the oxygen containing gas will be under pressure. In this connection, the oxygen can be in the form of the pure gas, or admixed with other inert gases including air itself, or compressed air, and the like.

Preferably, the oxygen is in the form of the pure gas and is used at a pressure ranging from atmospheric to just high enough above atmospheric to maintain a positive pressure of oxygen above the reaction mixture. The reaction mixture is preferably agitated by agitation means such as mechanical stirring.

The autoxidation is advantageously carried out within a temperature range of about 50° C. to about 250° C., depending largely on the catalyst employed, the anhydride solvent employed or the mixture thereof with acid and the rate of autoxidation desired. Preferably the oxidation is carried out at a temperature from about 100° C. to about 150° C.

The time required to effect the optimum conversion of aromatic hydrocarbon to phthalide will vary with the substrate employed and the anhydride/acid mixture etc. Again, this variable factor is not limiting in respect of the present invention but is easily determined by one skilled in the art by trial and error methods.

The progress of the autoxidation can be studied using any convenient analytical technique. However, a particularly simple and accurate method comprises removing an aliquot sample periodically from the reaction mixture and determining the proton nuclear magnetic resonance spectrum of the sample. The change and/or disappearance of the aliphatic protons adjacent to the aromatic ring and appearance of protons characteristic of the phthalide provides a rapid measure of the total mole percent conversion.

Another convenient means for analyzing the progress of the reaction, and, more particularly, the actual weight percent concentration of product versus starting material is the analysis of an aliquot sample by high pressure liquid chromatography (HPLC). (see Modern Practice of Liquid Chromatography edited by J. J. Kirkland, 1971, Wiley Intersciences Div. of John Wiley & sons, Inc., New York, N.Y.).

Other methods of monitoring the reaction are also useful such as thin layer chromatography (TLC) and gas/liquid chromatography (GPC).

Moreover, such analytical methods provide a simple means for determining when the autoxidation may be stopped conveniently as, for example, evidenced by the complete disappearance of the protons characteristic of the aliphatic ones adjacent to the aromatic ring.

The 3-alkanoyloxyphthalides produced in accordance with the above procedures can be easily isolated from the reaction mixtures and obtained in pure form by known methods. At the same time, if any polycarboxylic acid anhydrides are formed, they too can be isolated by known methods such as conversion to the sodium salts of the acid and extraction by water from the mixture and then converted to the free acid, or alternatively, if desired, back to the anhydride by known methods.

Illustratively, the solvent anhydride or mixture thereof with acid can be removed by distillation procedures and the phthalides and anhydrides isolated in crude form from which the pure materials can be removed from the catalyst and promoter by extraction by organic solvent followed by removal of the solvent by known methods.

Alternatively, the reaction mixture, including the solvent, can be treated with a non-solvent for the phthalide and anhydride causing them to precipitate as a solid, which is then collected by known filtration techniques.

The polycarboxylic acid anhydride can be separated by the extraction procedure noted above.

In a preferred embodiment to be discussed in detail below in connection with the combination of Methods A and B, the solvent(s) are simply removed by known distillation methods to provide a crude reaction product which contains the catalyst and promoter as impurity along with the phthalide and minor amount of polycarboxylic acid anhydride which crude reaction product is advantageously employed, without further treatment, in Method B for conversion of both products to the corresponding polycarboxylic acid.

Method B

The ionic oxidation of compounds (I) and (II) is carried out in aqueous alkaline hypohalite solution to form the corresponding carboxylic acids (III) and (IV). A particular advantage of the method is that the oxidation proceeds at low temperatures, even as low as room temperature and below.

Using the model 3-alkanoyloxyphthalide that was employed illustratively above, the ionic oxidation in accordance with the present invention can be represented schematically as follows.

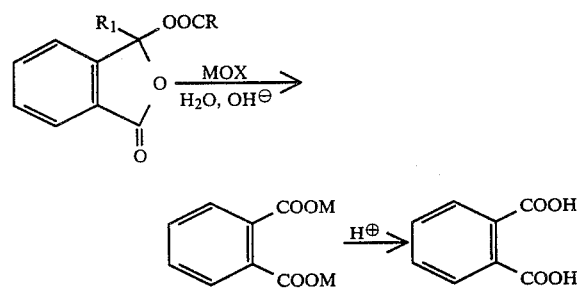

wherein R and $R_1$ are defined above and MOX represents a hypohalite reactant wherein X represents halogen such as chlorine, bromine, and iodine, and M represents an alkali or alkaline earth metal such as sodium, potassium, lithium, and calcium.

In a preferred embodiment of the Method B in accordance with the present invention the preferred class of novel diphthalides having the formula (II) above are oxidized to the corresponding tetracarboxylic acids (IV).

Particularly preferred embodiments are those wherein the starting diphthalides are the sulfonylbis(phthalides) and carbonylbis(phthalides) including isomer mixtures of the respective groups.

It will be obvious to one skilled in the art that the aromatic carboxylic acids produced in accordance with this method include such typical ones as phthalic acid, 4-halogenophthalic acid (such as chlorine, bromine, iodine, fluorine), 4-methoxyphthalic acid, trimellitic acid, pyromellitic acid, naphthalene-2,3-dicarboxylic acid, naphthalene-2,3,6,7-tetracarboxylic acid, acenaphthene-1,2-dicarboxylic acid, 2,2′,3,3′-biphenyltetracarboxylic acid, 3,3′,4,4′-biphenyltetracarboxylic acid, 3,3′-methylenebis(phthalic acid), 4,4′-methylenebis(phthalic acid), 3,3′,4,4′-diphenylethertetracarboxylic acid, 2,2′,3,3′-diphenylethertetracarboxylic acid, 2,2′,3,3′- diphenylsulfonetetracarboxylic acid, 3,3',4,4'-diphenyl-sulfonetetracarboxylic acid, 2,2',3,3'-benzophenonetetracarboxylic acid, 3,3',4,4'-benzophenonetetracarboxylic acid, and the like.

In the practice of this Method B, the 3-alkanoyloxyphthalide is made to disperse or preferably dissolve in an aqueous alkaline hypohalite solution and the resulting product is stirred. The reaction solution is maintained on the alkaline side throughout the course of the reaction in the manner described below.

The mode of operation in respect of whether the aqueous alkaline hypohalite is prepared in a separate step and added to the phthalide, or, alternatively, prepared in situ by the addition of the appropriate elemental halogen directly to the reaction solution of aqueous alkaline phthalide is purely optional. As far as ease of manipulation it is preferable to prepare the hypohalite in situ.

The hypohalite is advantageously employed within a range of about 0.75 to about 2.0 moles per equivalent of phthalide, and preferably within a range of from about 1.0 to about 1.5 moles per equivalent of phthalide wherein the equivalent weight of the phthalide is defined by its molecular weight divided by the number of phthalide rings in the molecule.

The hypohalite employed can be any one of the known materials which have been used in the prior art for carrying out ionic oxidations and is inclusive of sodium hypochlorite, sodium hypobromite, sodium hypoiodite, potassium hypochlorite, potassium hypobromite, potassium hypoiodite, calcium hypochlorite, calcium hypobromite, and calcium hypoiodite. Preferred amongst the illustrative examples above are sodium hypochlorite, potassium hypochlorite, and calcium hypochlorite.

As noted previously, it is preferred to prepare the hypohalite in situ simply by adding the halogen reagent, for example chlorine, into a solution of the phthalide in aqueous base until an amount required to prepare a predetermined proportion of hypohalite has been reached.

The aqueous base can be any of the strong inorganic bases known to those skilled in the art and typical of such reagents are sodium hydroxide, potassium hydroxide, lithium hydroxide, and the like. Conveniently, the base reagent and the hypohalite have the same cation which is the case when the hypohalite is prepared in situ.

The specific amounts of basic reagent to be employed to keep the solution alkaline will vary somewhat depending on such factors as the number of phthalide rings to be oxidized, whether the hypohalite is to be generated in situ, and the like. However, it is a simple matter to determine the requisite amount of base to maintain the alkalinity of the reaction solution and adjust it accordingly.

Simply as a guide but not a limiting amount, the base reagent can be employed at a level of at least about 4 equivalents per equivalent of phthalide. The presence of excess is particularly advantageous when the hypohalite is prepared in situ because of the consumption of base in the preparation of the hypohalite. For example, two equivalents of sodium hydroxide are required for every equivalent of sodium hypochlorite prepared from reaction with chlorine.

The oxidation is carried out in any suitable vessel capable of being stirred and heated. The temperature at which the ionic reaction is performed is surprisingly mild and will vary somewhat depending on the starting phthalide, particularly its purity and the presence of ingredients which appear to have a catalytic effect on the oxidation and which ingredients and the circumstances of their presence will be discussed below. Advantageously, the oxidation is carried out at a temperature of from about 0° C. to about 100° C., and preferably from about 20° C. to about 75° C.

The progress of the oxidation can be followed using the same analytical procedures described above for Method A. TLC analysis serves as a simple and rapid means for determining the progress and completion of the reaction. Advantageously, the reaction is completed within a period of from about 1 hour to about 8 hours, preferably from about 1 hour to about 4 hours.

As noted above the polycarboxylic acid is obtained directly, and, most easily, simply by neutralizing the basic reaction solution with any acid reagent capable of neutralizing the base. The free carboxylic acids, generally speaking, precipitate directly from the aqueous solution as crystalline products which are easily collected by standard filtration techniques.

It should be noted that both an isomer mixture and a single form of the phthalide starting material produce the same polycarboxylic acid product.

Further, it should be noted that, if the mixture to be oxidized consists of phthalide(s) and its(their) corresponding polycarboxylic acid anhydride(s), the sole product(s) is(are) the corresponding polycarboxylic acid(s).

Combination of Method A and Method B

Although the starting phthalides (I) and (II) used in the oxidation Method B can be obtained via alternate synthetic routes, the Method A described above provides the materials in unexpectedly high yield and purity. Furthermore, the side-product obtained, namely the acid anhydride of the polycarboxylic acid, serves as a perfect starting material in Method B because it becomes part of the polycarboxylic acid yield along with the same polycarboxylic acid formed from the phthalide.

In an optional, but much preferred, embodiment of the overall oxidation of aromatic hydrocarbons (V) and (VI) to the corresponding polycarboxylic acid (III) and (IV) it has been discovered, quite surprisingly, that Method A and B can be combined in such a way that the Method B oxidation can be carried out at room temperature and still provide the acids in high yields.

Illustratively, after the autoxidation of the aromatic hydrocarbon has been completed in accordance with Method A set forth above, the reaction solution is treated to remove the solvent, for example, by distillation.

The crude reaction mixture obtained can be in the form of an oil or semi-solid, and, in some cases a crystalline mass. It still contains the heavy metal oxidation catalyst and promoter. This crude reaction mixture containing the phthalide, the catalyst and promoter, and, any polycarboxylic acid anhydride which may have formed, is used directly in the Method B oxidation described above.

Although the ionic oxidation can be carried out at any temperature within the range set forth above (i.e. 0° to 100° C.), it has been found that the oxidation proceeds rapidly at ambient room temperature (about 20° C.).

The catalyst and promoter combination which seems to provide the preferred enhancement of the Method B is the combination of at least one heavy metal acetate and at least one bromide ion promoter such as sodium, potassium, and lithium bromide. Most preferred amongst these groups is the combination of cobalt acetate with sodium bromide.

The polycarboxylic acids obtained in accordance with the present invention have the various utilities noted above. In particular, they are readily converted to the acid anhydride using any of the standard methods employed for such a conversion. Typically, the acids can be heated under reflux in organic solvents, as for example, 1,2,4-trichlorobenzene or 1,2-dichlorobenzene and the water formed by the anhydride formation removed using a Dean-Stark trap.

The anhydrides are particularly useful in the preparation of polymers such as polyamides, polyamideimides, polyimides and the like.

The following examples describe the manner and process of making and using the invention and set forth the best mode contemplated by the inventor for carrying out the invention but are not to be construed as limiting.

EXAMPLE 1

A three-necked flask was provided with a condenser, a thermometer, and a gas inlet tube and was charged with 24.0 g. (0.1008 mole) of 3,3′,4,4′-tetramethylbenzophenone which was 97 to 98 percent pure, 1.6 g. (0.0064 mole) of cobaltous acetate tetrahydrate, 0.8 g. (0.0078 mole) of sodium bromide, 80 g. (0.784 mole) of acetic anhydride, and 120 ml. of glacial acetic acid.

The reaction mixture, which was a suspension at room temperature, was stirred and heating with an oil bath was initiated. The mixture soon became a homogeneous solution and starting at 60° C. a stream of oxygen at a rate of about 150 to 200 ml. per minute was passed into the solution. The oil bath was maintained at a temperature of 150° C. to 155° C. which resulted in a solution temperature of 120° C. to 125° C.

After 7 hours the solution temperature dropped to 115° C. Thin layer chromatography (TLC) of an aliquot sample which was spotted on a silica gel plate (5 cm × 10 cm KF5 plate supplied by Whatman Filter Co., Clifton, N.J.) and developed with a 6/4 parts by weight solution of ethyl acetate and cyclohexane showed the presence of 3 components (by ultaviolet light) corresponding to the three geometric isomers of 5,5′-, 5,6′-, and 6,6′-carbonylbis(3-acetoxyphthalide). Another aliquot, taken at same time, spotted on a TLC plate and developed with a 7/3 mixture of ethyl acetate and acetic acid showed two components corresponding to 3,3′,4,4′-benzophenonetetracarboxylic acid dianhydride and the hydrolyzed 3,3′,4,4′-benzophenonetetracarboxylic acid.

The autoxidation solution was poured into 400 ml. of ice cold water during stirring. A white solid precipitate was formed which was isolated by filtration, washed with ice water and pressed and dried to provide a white solid autoxidate product; wt.=38.0 g. Proton NMR showed a sharp singlet at $\delta 7.56$ (benzylic proton), and two closely situated singlets at $\delta 62.20$ and 2.16 (acetate protons). Based on the ratio of aromatic protons to benzylic protons the isolated autoxidate was a 70/30 mole percent mixture of the 3 phthalide isomers noted above and 3,3′,4,4′-benzophenonetetracarboxylic acid dianhydride respectively.

The 38.0 g. of solid autoxidate was transferred to a three-necked flask equipped with a high speed mechanical stirrer, a thermometer and a condenser. To the flask was added 300 ml. of aqueous alkaline sodium hypochlorite in one portion. The hypohalite had been previously prepared by passing 12.2 g. (0.172 mole) chlorine into a sodium hydroxide solution [prepared from 42.0 g. (1.05 mole) of sodium hydroxide dissolved in 300 ml. water]. The reaction solution was stirred at ambient temperature (circa 20° C.) for 2 hours, followed by stirring at 50°–55° C. for 1 hour.

The cooled solution was acidified with 75 ml. concentrated hydrochloric acid, cooled in ice, and seeded with a sample of 3,3′,4,4′-benzophenonetetracarboxylic acid. A white solid precipitate of the 3,3′,4,4′-benzophenonetetracarboxylic acid formed. The crystalline product was collected by filtration, washed with 30 to 40 ml. of ice-cold water, and dried in an oven at 100° C.; dry product wt.=30.0 g. (83.1% yield based on the tetramethylbenzophenone); m.p. 218°–220° C. (dec.).

The autoxidation reaction described above was repeated using the same ingredients, proportions, and conditions, up to the end of the 7 hour reaction period. At this point the reaction solution was heated at 50° C. under aspirator pressure (about 10 mm of mercury pressure) and the solvent stripped off.

A residue of 47.0 g. of crude reaction mixture in the form of tarry viscous material remained. This residue was subjected to the same ionic oxidizing conditions set forth above using the same concentration of alkaline sodium hypochlorite.

The reaction solution was stirred briskly to dissolve the tarry residue at 15° C. for one hour followed by room temperature (circa 20° C.) for 3 hours.

A black precipitate of cobalt oxide was removed by filtering with Celite Filter Aid (supplied by Johns-Manville Products Corp., Lompoc, Cal.). The filtrate was acidified with 75 ml. conc. hydrochloric acid and seeded with 3,3′,4,4′-benzophenonetetracarboxylic acid. The precipitated 3,3′,4,4′-benzophenonetetracarboxylic acid product was collected and dried at 100° C.; wt.=32.0 g. (88.7% yield based on starting tetramethylbenzophenone); m.p. 218°–220° (dec.).

EXAMPLE 2

Using the procedure and apparatus set forth above in Example 1, the autoxidation of 3,3',4,4'-tetramethylbenzophenone was repeated except that the proportions of all the reactants were halved. After the 7 hour reaction period had elapsed the solvent was stripped off in vacuo according to the method described above to provide 23.9 g. of autoxidate residue.

The residue was scraped and transferred to a reaction flask equipped as described above in Example 1 for the ionic oxidation. Sodium hydroxide solution prepared from 23 g. of sodium hydroxide dissolved in 175 ml. of water was added to the flask and stirred at 15° C. for 1 hour using a cooling bath. Chlorine (6 g.) was passed into the stirred solution and after the addition was completed the cooling bath was removed.

The solution was stirred for 3 hours at room temperature (circa 20° C.) during which period the temperature reached 32° C. after one hour and slowly receded to 27° C. A TLC analysis of an aliquot as described above in Example 1 on silica gel and development in 7/3 ethyl acetate/acetic acid showed that the reaction was complete.

The solution was filtered to remove the black cobalt oxide and the filtrate acidified with 36 ml. of conc. hydrochloric acid. After seeding with pure 3,3',4,4'-benzophenonetetracarboxylic acid and standing at room temperature (20° C.) the product of 3,3',4,4'-benzophenonetetracarboxylic acid precipitated and was collected and dried to constant weight=16.6 g. (92.2% yield based on starting tetramethylbenzophenone).

EXAMPLE 3

Using the apparatus and procedure described in Example 1, 12.0 g. (0.0504 mole) of 3,3',4,4'-tetramethylbenzophenone of 99% purity was autoxidized using 1.0 g. (0.004 mole) of cobaltous acetate tetrahydrate, 0.5 g. (0.005 mole) of sodium bromide and 100 ml. of acetic anhydride. The oxygen was passed into the solution at a rate of about 100 ml./minute during stirring and while heating the solution in an oil bath.

The reaction temperature after 20 minutes was about 130° C. and, over a period of about 4 hours with a reaction temperature of about 124° C., the oxidation was shown to be complete by the TLC analysis method set forth above using the silica gel plate and development solution of 6/4 ethyl acetate/cyclohexane. The products shown to be present were the 5,5'-, 5,6'-, and 6,6'-carbonylbis(3-acetoxyphthalide) isomer mixture and 3,3',4,4'-benzo-phenonetetracarboxylic acid dianhydride.

The resulting blue solution was diluted with water, extracted with ethyl acetate and the organic layer separated and dried by storage over magnesium sulfate. Removal of solvent in vacuo on a rotary evaporator under aspirator pressure followed by vacuum pump pressure yielded 20.0 g. of tarry residue. Proton NMR showed the residue to be a 75/25 mole percent mixture of the 5,5'-, 5,6'-, and 6,6'-carbonylbis(3-acetoxyphthalide) isomer mixture and 3,3',4,4'-benzophenonetetracarboxylic acid dianhydride. The overall yield of oxidized products was 100%.

EXAMPLE 4

Using the apparatus and procedure described in Example 1, 13.7 g. (0.05 mole) of 3,3',4,4'-tetramethyldiphenylsulfone of 88.9% purity was autoxidized using 1.0 g. (0.004 mole) of cobaltous acetate tetrahydrate, 0.5 g. (0.005 mole) of sodium bromide and 100 ml. of acetic anhydride. The oxygen was passed into the solution at a rate of about 100 ml./minute during stirring and while maintaining the solution at a temperature of 120° C. to 127° C.

After a 3 hour reaction period, the solution was cooled and the solvent removed in vacuo to yield a semi-solid residue.

The semi-solid autoxidate residue was transferred to a reaction flask equipped as described above in Example 1 for the ionic oxidation. A 175 ml. portion of aqueous alkaline sodium hypochlorite was added to the residue. The hypohalite had been previously prepared by passing 7.1 g. of chlorine into a solution of 22 g. of sodium hydroxide dissolved in 175 ml. of water.

The reaction flask was cooled to 10° C. to 15° C. by means of a cooling bath and stirred for about 1 hour to dissolve the autoxidate residue. The cooling bath was removed and the solution stirred at room temperature (circa 20° C.) for 2 hours during which time the solution temperature reached 45° C. and then receded to 32° C. TLC analysis of an aliquot sample indicated that the oxidation was completed after 1 hour.

A black precipitate of cobalt oxide was removed by filtration and the filtrate was acidified with 37 ml. of conc. hydrochloric acid. Upon cooling, a white crystalline precipitate of the 3,3',4,4'-diphenylsulfonetetracarboxylic acid was formed. It was isolated by filtration, washed with a 10 percent sodium chloride solution, then dried at 100° C.; wt.=14.0 g. (81% yield based on the adjusted weight of pure starting tetramethyldiphenylsulfone); m.p. 240° C.-244° C. (dec.); $^{13}$C NMR confirmed the structure as the 3,3',4,4'-diphenylsulfonetetracarboxylic acid.

EXAMPLE 5

Using the apparatus and procedure described in Example 1, 10.6 g. (0.10 mole) of o-xylene was autoxidized using 1.0 g. (0.004 mole) of cobaltous acetate, 0.5 g. (0.005 mole) of sodium bromide and 100 ml. of acetic anhydride. The oxygen was passed into the solution at a rate of about 100 ml./minute during stirring and while heating the solution at a temperature of 110° C. to 122° C.

After 3 hours gas liquid chromatography (GLC) analysis of an aliquot sample showed the presence of two components equivalent to a 60 weight percent proportion of 3-acetoxyphthalide and 40 weight percent proportion of phthalic anhydride.

Continuation of the oxidation for a further period of about 1.5 hours resulted in a change of the weight concentrations of the above two products to 56 percent and 44 percent respectively.

The reaction solution was diluted with water, extracted with ethyl acetate, the organic layer washed with water, then dried by storage over anhydrous magnesium sulfate. Evaporation of the solvent in a rotary evaporator under aspirator pressure and a warm water bath provided a crystalline solid residue; wt.=15.0 g. (GLC analysis showed a 55/45 weight percent proportion of 3-acetoxyphthalide to phthalic anhydride; proton NMR and GLC comparisons with authentic samples confirmed the identities of these two products); yield of 3-acetoxyphthalide=42.9%; yield of phthalic anhydride=45.6%.

The mixture of 3-acetoxyphthalide and phthalic anhydride is oxidized by the ionic oxidation procedure set forth in Example 1 using aqueous alkaline sodium hypochlorite solution. Acidification with concentrated hydrochloric acid and cooling of the resulting reaction mixture provides the precipitated phthalic acid.

I claim:

1. A method for converting a 3-alkanolyloxyphthalide selected from the formulae consisting of

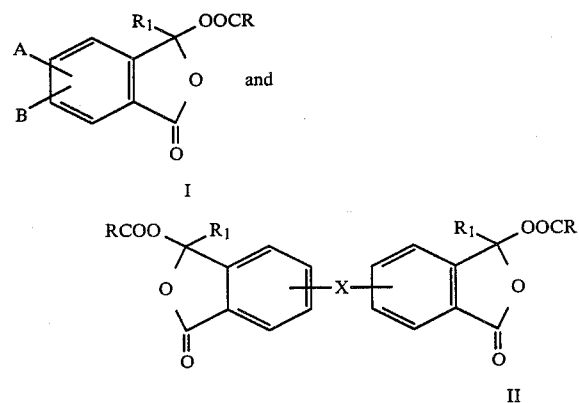

to the corresponding polycarboxylic acids having the formulae

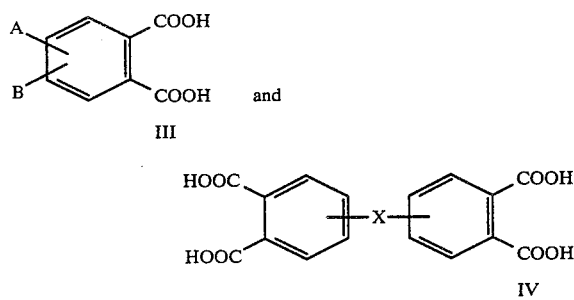

wherein R represents lower-alkyl, $R_1$ is selected from the group consisting of hydrogen and linear lower-alkyl, A and B taken separately are independently selected from the group consisting of hydrogen and any substituent that does not react with the carboxylic acid products or phthalides or otherwise interfere with the oxidation, A and B taken together represent an aromatic nucleus fused to the phenyl ring, and X is selected from the group consisting of —CO—, —SO$_2$—, —O—, and a single bond, said method comprising oxidizing said 3-alkanoyloxyphthalide with aqueous alkaline hypohalite.

2. A method according to claim 1 wherein said hypohalite is sodium hypochlorite.

3. A method according to claim 1 wherein an alkanoyloxyphthalide having the formula (II) wherein $R_1$ is hydrogen is converted to the corresponding tetracarboxylic acid (IV).

4. A method according to claim 3 wherein X is —CO—.

5. A method according to claim 3 wherein X is —SO$_2$—.

6. A method according to claim 3 wherein R is methyl and said oxidation is carried out with aqueous alkaline sodium hypochlorite at a temperature of from about 20° C. to about 75° C.

7. A method according to claim 6 wherein a mixture of isomers comprising 5,5'-, 5,6'-, and 6,6'-carbonylbis(3-acetoxyphthalide) is converted to 3,3',4,4'-benzophenonetetracarboxylic acid.

8. A method according to claim 6 wherein a mixture of isomers comprising 5,5'-, 5,6'-, and 6,6'-sulfonylbis(3-acetoxyphthalide) is converted to 3,3',4,4'-diphenylsulfonetetracarboxylic acid.

9. A method in accordance with claim 1 wherein said 3-alkanoyloxyphthalide employed as starting material is prepared by autoxidizing with oxygen in a solution comprising an anhydride of an aliphatic monocarboxylic acid having 2 to 8 carbon atoms in the presence of a heavy metal oxidation catalyst and a promoter an aromatic compound selected from the formulae consisting of

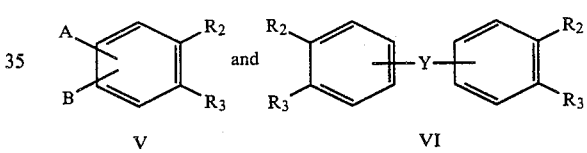

wherein $R_2$ and $R_3$ are independently selected from linear lower-alkyl, A and B when taken separately are independently selected from the group consisting of hydrogen and any substituent that does not react with the carboxylic acid products or phthalides or otherwise interfere with the oxidation, A and B when taken together represent an aromatic nucleus fused to the phenyl ring, and Y is selected from the group consisting of —CO—, —SO$_2$—, —O—, a single bond, and —CH$_2$—.

10. A method according to claim 9 wherein 3,3',4,4'-tetramethylbenzophenone is converted to 3,3',4,4'-benzophenonetetracarboxylic acid by
   (a) autoxidizing said 3,3',4,4'-tetramethylbenzophenone with oxygen at a temperature of from about 100° C. to about 125° C. in a solution comprising a mixture of acetic acid and acetic anhydride in the presence of cobaltous acetate catalyst and sodium bromide promoter to form a crude reaction mixture comprising a major proportion of a mixture of 5,5'-, 5,6'-, and 6,6'-carbonylbis(3-acetoxyphthalide) and a minor proportion of 3,3',4,4'-benzophenonetetracarboxylic acid dianhydride;
   (b) removing said acetic acid and acetic anhydride from said crude reaction mixture; and
   (c) oxidizing said crude reaction mixture with aqueous alkaline sodium hypochlorite to form said 3,3',4,4'-benzophenonetetracarboxylic acid.

* * * * *